United States Patent [19]

Roberson, Jr.

[11] Patent Number: 5,593,449
[45] Date of Patent: Jan. 14, 1997

[54] DUAL TAPER STEM EXTENSION FOR KNEE PROSTHESIS

[75] Inventor: Raymond H. Roberson, Jr., Bartlett, Tenn.

[73] Assignee: Smith & Nephew Richards Inc., Memphis, Tenn.

[21] Appl. No.: 206,515

[22] Filed: Mar. 4, 1994

[51] Int. Cl.$^6$ .................................................. A61F 2/38
[52] U.S. Cl. ........................... 623/20; 623/18; 623/22; 606/60
[58] Field of Search ............................. 623/18, 19, 20, 623/21, 22; 606/60, 62

[56] References Cited

U.S. PATENT DOCUMENTS

| | | | |
|---|---|---|---|
| 4,714,471 | 12/1987 | Grundei | 623/20 |
| 4,822,366 | 4/1989 | Bolesky | 623/20 |
| 4,936,853 | 6/1990 | Fabian et al. | 623/20 |
| 4,985,037 | 1/1991 | Petersen | 623/20 |
| 5,002,581 | 3/1991 | Paxson et al. | 623/23 |
| 5,061,271 | 10/1991 | Van Zile | 623/20 |
| 5,133,760 | 7/1992 | Petersen et al. | 623/20 |
| 5,152,796 | 10/1992 | Slamin | 623/20 |
| 5,194,066 | 3/1993 | Van Zile | 623/20 |
| 5,282,865 | 2/1994 | Dong | 623/19 |
| 5,286,260 | 2/1994 | Bolesky et al. | 623/18 |
| 5,290,313 | 3/1994 | Heldreth | 623/20 |
| 5,358,526 | 10/1994 | Tornier | 623/18 |

FOREIGN PATENT DOCUMENTS

545833A1  11/1992  European Pat. Off. .

*Primary Examiner*—Paul B. Prebilic
*Attorney, Agent, or Firm*—Pravel, Hewitt, Kimball & Krieger

[57] ABSTRACT

A knee prosthesis for surgical implantation to a patient's leg bone at the knee joint area includes a prothesis body portion that extends transversely relative to the patient's intramedullary canal for carrying a bearing surface that articulates with the patient's adjacent leg bone or with another prosthesis component. A conical connector extends from the prosthesis portion and along an axis that generally tracks the patient's intramedullary canal. A stem member includes first and second end portions and has a central longitudinal stem axis. The stem member includes a socket at each end portion for forming connections to the conical connector at the respective end portions as selected by the surgeon. One of the sockets has a central longitudinal axis that generally coincides with the central longitudinal axis of the stem. The other socket has a central longitudinal axis that forms an acute angle with the axis of the stem.

19 Claims, 3 Drawing Sheets

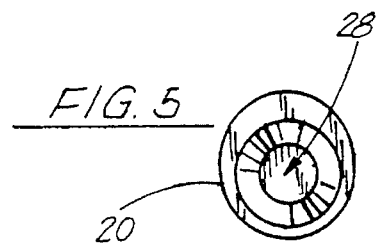
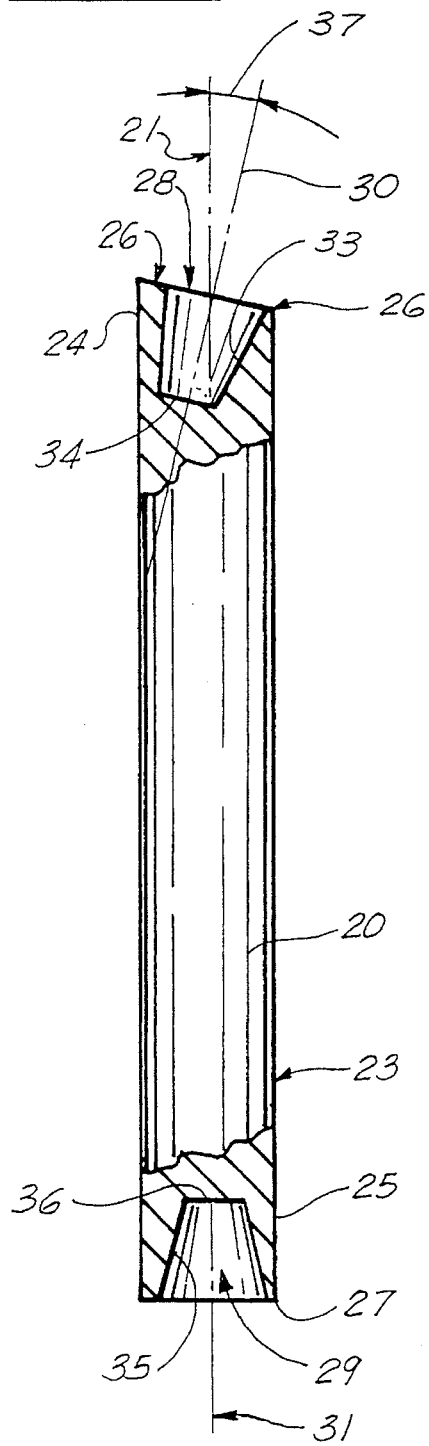
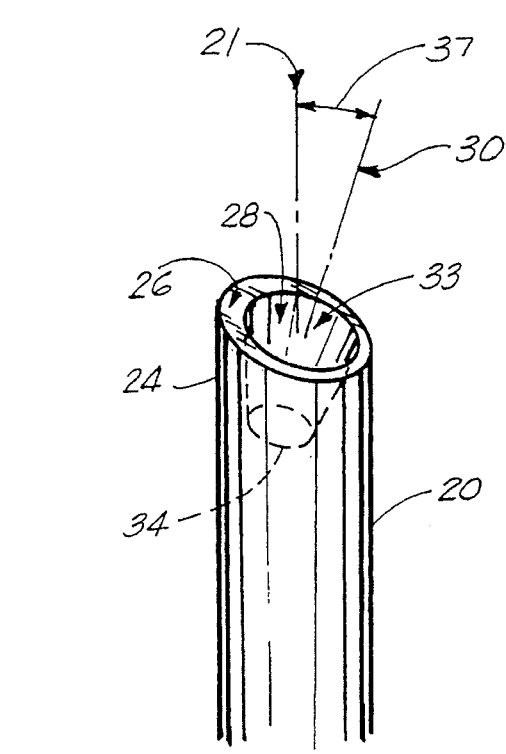
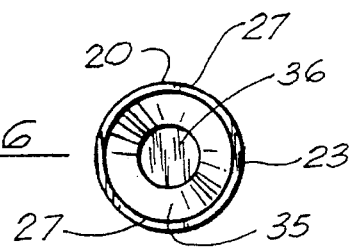

DUAL TAPER STEM EXTENSION FOR KNEE PROSTHESIS

BACKGROUND OF THE INVENTION

1. Field Of The Invention

The present invention relates to orthopedic prosthetic devices and more particularly relates to a modular joint prosthesis. Even more particularly, the present invention relates to an improved orthopedic joint implant that allows the surgeon to choose intraoperatively, the valgus angle for a stem extension that will best fit the patient's intramedullary canal by using a stem member having two tapers, one at each end of the stem and each taper having a different angle in relation to the central longitudinal axis of the stem itself. The apparatus of the present invention thus provides an easy method and apparatus for selecting the valgus angle, simply using one end or the other depending on the desired angle.

2. General Background

Most orthopedic implants that have an extension that fits into the intramedullary canal of a patient's bone provide a fixed position for the extension relative to the joint prosthesis that can not be changed intraoperatively. However, some prior art type joint implants do provide variable valgus angles. The prior art typically solves this problem by placing the variable angle structure at one end of the stem only. By only providing a variability at one end of the stem, a complicated system is necessarily required in order to change the angle. Many different components and/or complicated linkage can be required to achieve the desired result.

Many joint prosthetic devices have been patented which have discussed the problem of changing the valgus angle intraoperatively.

U.S. Pat. No. 5,152,796 uses a series of bolts extending through a femoral component at different angles that will correspond to different valgus angles. The loosening of a bolt could lead to catastrophic failure of the entire component. Any prosthesis system of the '796 patent includes stems of different lengths and different diameters which can be attached to the bolts to provide a system with stems of different and diameter lengths set at different valgus angles.

U.S. Pat. No. 5,133,760 provides a modular prosthesis stem extension that is discussed as being an improvement over U.S. Pat. No. 4,985,037. A stem extension is disclosed with a six degree valgus inclination as well as a degree of superior or inferior angulation such as for example two (2°) degrees. This inclination and angulation are anatomically correct in each reversed position of the modular stem extension. The '760 patent discloses a coupling mechanism and a stem with an off-set angle at one end that goes through the coupling. This allows the stem to be rotated at different positions for different angles, then locked into place with a locking nut. There is a possibility of loosening at the locking mechanism which could lead to instability and failure of the prosthesis.

U.S. Pat. No. 5,002,581 issued to Paxxon entitled "Modular Hip Joint Prosthesis with Adjustable Anteversion" provides a modular hip prosthesis and instrumentation for implanting same. The hip prosthesis has provision for varying the angulation between the stem portion and the trochanteral module portion by provision of connection means between the neck and stem which can be positioned or attached together in a variety of rotational positions. Variation of the angulation or anteversion is made possible in the virtue of the fact that the axis of the connection portion of the stem and neck is angularly off-set from the axis of the body of the stem and neck respectively. Instrumentation is provided for formation of a cavity for implantation of a prosthesis which is provided within indication means for indicating to the surgeon the optimum angle for the assembly of the prosthesis for implantation into a particular proximal femur. A problem can occur with this system when rotating the stem as translation of the stem is not only in the desired medial-lateral direction, but also to the anterior or posterior direction, depending on the angle desired. This could result in impingement of the stem with the cortex and the canal in the anterior or posterior position.

U.S. Pat. No. 4,985,037 issued to Peterson provides a universal modular prosthesis stem extension designed to be attachable on the under surface of a femoral or tibial prosthesis. The stem extension forms part of a modular system wherein a single stem extension could be selectively attached to any one of a multiplicity of femoral or tibial components, thus reducing the amount of inventory which is necessary to be maintained by a surgeon. In the preferred embodiment, each stem extension is designed with a six (6°) degree valgus inclination and is reversible for left or right patients. The system is held in place with pins that could loosen during use. Because a single stem must be required for each different angle, increased inventory is required.

U.S. Pat. No. 4,822,366 issued to Bolesky provides a modular knee prosthesis assembly for the replacement of a portion of the knee joint. The assembly has a femoral component which is formed to include first bearing surfaces and first means for demountably receiving at optional femoral system member. The assembly also has a tibial component that is formed to include a platform and second means for demountably receiving an optional tibial stem member. The assembly includes a separate tibial insert that is configured to be supported by the tibial component platform. The tibial insert is formed to include second bearing surfaces that are configured to mate with the first surfaces on the femoral component to permit pivotal movement between the femoral component and the tibial component. This system puts a stem with the reduced diameter into a mating counter bore of a mounting fixture which is then affixed to the component by means of a screw or nut on the side of the component opposite the stem mounting fixture. As the screw or nut is tightened the component is sandwiched between the screw or nut in the stem mounting fixture. A problem can occur in that this system provides no locking mechanism to prevent rotation of the stem which in turn can cause loosening of the screw or nut or loss of fixation of the entire component.

A French patent 0545833A1 allows the stem to be shifted to align with an intramedullary canal property. However, the French '833 patent does not provide variable valgus angle as provided by the present invention.

SUMMARY OF THE PRESENT INVENTION

The present invention allows the surgeon to choose intraoperatively the valgus angle for a stem extension that will best fit the patient's intramedullary canal. This is achieved by having two tapers, one at each end of the stem. Each taper has a different angle in relation to the central longitudinal axis of the stem itself.

The apparatus of the present invention thus provides an easy way to select the valgus angle simply selecting one end or the other of the stem. This provides a system for varying the valgus angle which reduces costs, reduces inventory, and reduces operating time in that fewer sterilizations of instruments are needed. The present invention thus provides an improved knee or hip or like prosthesis for surgical implantation to a patient's leg bone at the knee joint.

The apparatus includes a prosthesis body portion that extends transversely relative to the patient's intramedullary canal for carrying a bearing surface that articulates with the patient's adjacent leg bone (or acetabulum) or with another prosthesis component.

A conical connector extends from the prosthesis portion and along an axis that generally tracks the patient's intramedullary canal.

A generally cylindrically shaped stem member provides first and second end portions and has a central longitudinal stem axis. Each stem member has a socket for connecting to the conical connector.

One of the sockets includes a central longitudinal axis that could generally coincide with the central longitudinal axis of the stem. However, the first socket could be angled relative to the longitudinal axis of the stem.

A second socket at the opposite end portion of the stem has a central longitudinal axis that forms an angle with the stem axis. The stem extension member could provide tapers at each end, each with its own taper axis that adds some desired angle to the axis of the stem. Other types of connections could be used such as hexagonal connections, threaded connections or the like. A central, longitudinal cannulation could be provided for allowing a threaded attachment member to extend through the cannulation.

The present invention can be used as an extension for any number of orthopedic prosthetic devices including for example femoral and tibial knee components and hip femoral components.

The apparatus of the present invention allows for lengthening of existing stems on these components, while providing a variability of the valgus angle so that the natural valgus of the femur can be approximated as closely as possible.

Each of the tapers has a central axis that is at some known angle to the central longitudinal axis of the stem extension itself. This allows the surgeon to change, intraoperatively, the valgus angle of the stem extension and more closely follow the intramedullary canal of a patient.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 3 is a sectional fragmentary view of the preferred embodiment of the apparatus of the present invention illustrating the stem portion thereof.

FIG. 4 is a partial perspective view of the preferred embodiment of the apparatus of the present invention illustrating the stem portion thereof; and FIG. 5–6 are fragmentary views of the preferred embodiment of the apparatus of the present invention illustrating steam socket portions thereof.

DETAILED DESCRIPTION OF THE PREFERRED EMBODIMENT

Figure 1:
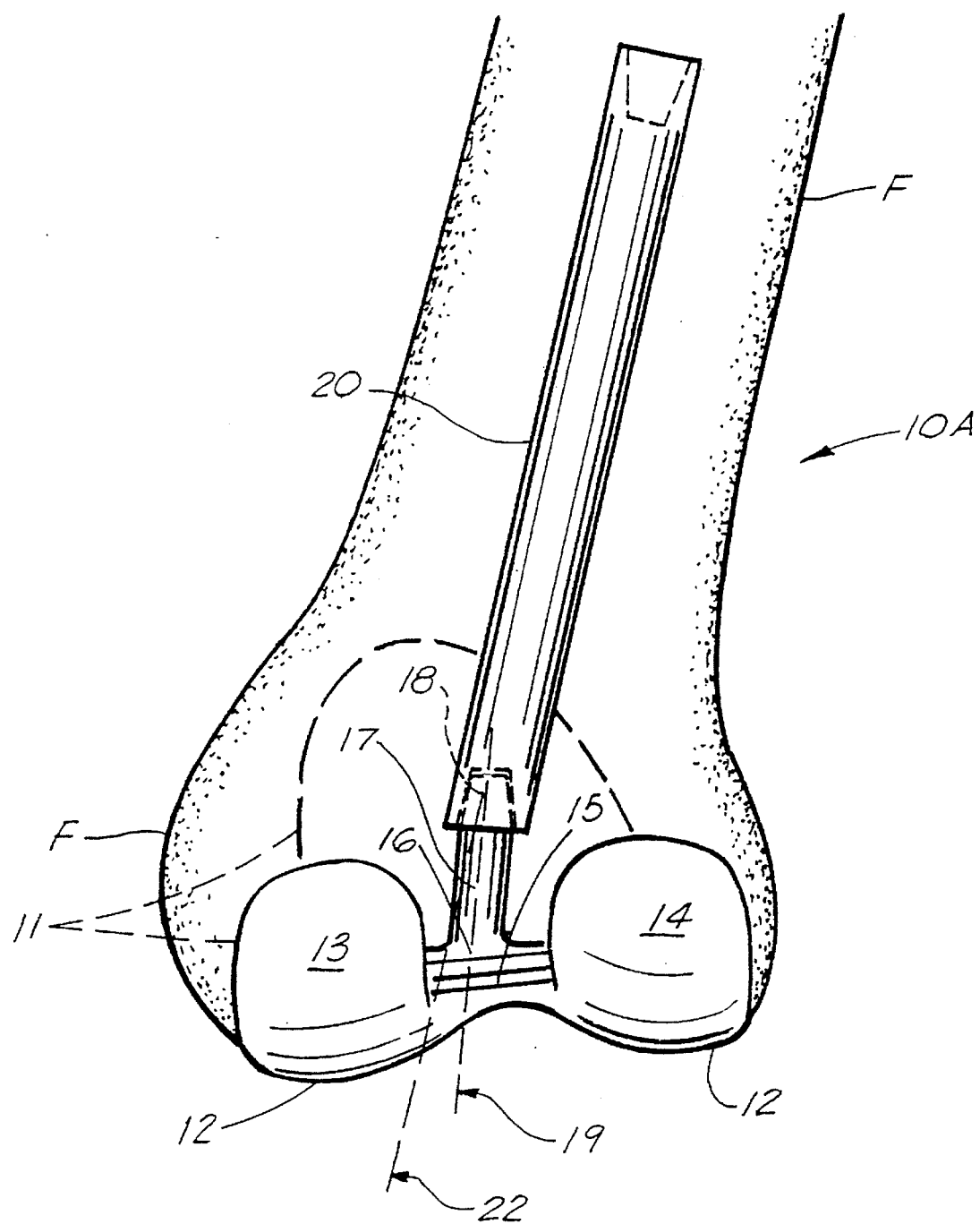
FIG. 1 is a perspective view of the preferred embodiment of the apparatus of the present invention illustrating a femoral component of a knee prosthesis.

FIG. 1 shows a knee prosthesis 10A that includes a femoral component 11 having an articulating surface 12 that includes a pair of condylar portions 13, 14. At the rear surface 15 of knee prosthesis 10A, a conversion module 16 can be used as an interface between the articulating surface 12 portion of femoral component 11 and a stem 20 portion that extends into the intramedullary canal of the patient's femur F during use. Such a conversion module can be seen in U.S. Pat. No. 4,950,298 entitled "Modular Knee Joint Prosthesis" issued to Ramon Gustilio, James A. Rand, Jeffrey Roberts and Jennifer J. Lackey, incorporated herein by reference.

Stem connector 17 extends from the rear surface of conversion module 16. Stem connector 17 includes a frustroconical portion 18 that extends along a connector axis 19. Stem 20 has socket portions as will be described hereinafter that are correspondingly shaped and sized to form a morse taper or wedge lock connection with frustroconical portion 18 of stem connector 17.

In FIG. 3, stem 20 is shown as being generally cylindrically shaped having a cylindrically shaped outer surface 23 and a central longitudinal axis 21.

At one end portion 25 of stem 20, socket 29 is shown as being a generally frustroconically shaped socket portion. Socket 29 communicates with transverse end surface 27 of stem 20. Socket 29 is defined by a conically shaped inner surface 35 and a circular transverse end surface 36. Socket 29 provides a socket axis 31 that is coincident with the central longitudinal axis 21 of stem 20. A neutral stem axis 21 defines an axis that coincides with connector axis 19.

Opposite socket 29 is socket 28 which is also frustroconically shaped. Socket 28 is defined by an inner conically shaped surface 33 and circular end wall 34. Socket 28 communicates with annular end surface 26. The socket 28 has a central longitudinal taper axis 30 that forms an angle with the central longitudinal axis 21 of stem 20, the neutral stem axis.

End portion 24 of stem 20 has angled socket 28 and also annular surface 26 which forms a plane that is angled relative to cylindrical outer surface 23. In FIG. 3, angle 37 defines the angle between socket axis 30 and central longitudinal axis 21 of stem 20. The outer surface 23 at the end portions 24, 25 can be conically shaped, tapering toward a smaller diameter at the ends of stem 20.

Figure 2:
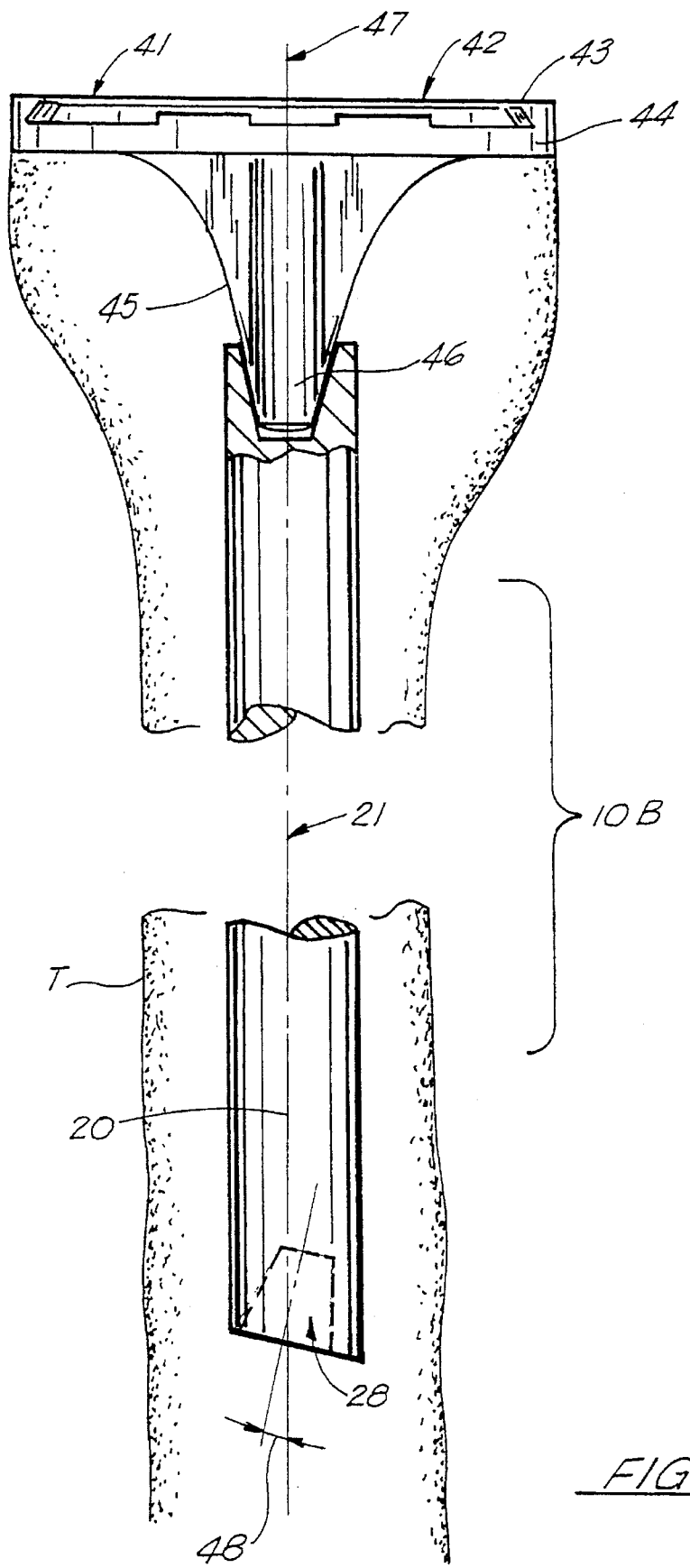
FIG. 2 is a perspective view of the preferred embodiment of the apparatus of the present invention illustrating a tibial component of the knee prosthesis.

In FIG. 2, joint prosthesis 10B includes tibial component 40 having articulating surfaces 41, 42 for receiving a tibial component during use. The articulating surfaces 41, 42 are concave portions of polymeric insert 43. Polymeric 43 is placed on metallic table 44 and held thereon using a dove tail type connection or the like. Table 44 has a rear connector portion 45 that includes frustroconical connector 46. A surgeon can select a particular socket 28 or 29 to obtain a desired valgus angle when placing prosthesis 10B in the intramedullary canal of the patient's tibia T. Frustroconical connector 46 has a central longitudinal axis 47 that is coincident with the neutral stem axis 21.

Central longitudinal axis 21 of stem 20 is coincident with connector axis 47 when stem 20 is attached to frustroconical connector 46 by placing the socket 29 upon connector 46. Socket 29 and axis 31, can be coincident with stem axis 21. Alternatively, socket 29 and axis 31 can be offset with respect to stem axis 21 so that both axis 30 and axis 31 are angled relative to stem axis 21.

An angular orientation is obtained between stem axis 21 and connector axis 47 when stem 20 is connected to connector 46 at socket 27. This produces an offset orientation of stem axis 21 and axis 47 of connector 45. In FIG. 2, the angle 48 defines an angle between socket axis 30 and stem axis 21 when the stem 20 is connected to table 44 by placing socket 28 upon connector 46. The angle 48 is preferably between zero and ten degrees (0°–10°).

The femoral component 11 can be provided with any connector axis 19, defining the orientation of connector 17 with reference to condylar 13, 14. Likewise, table 44 can be provided with any orientation of connector 46 relative to articulating surfaces 41, 42.

The following table lists the part numbers and part descriptions as used herein and in the drawings attached hereto.

PARTS LIST

| Part Number | Description |
| --- | --- |
| F | femur |
| T | tibia |
| 10A | joint prosthesis |
| 10B | joint prosthesis |
| 11 | femoral component |
| 12 | articulating surface |
| 13 | condylar portion |
| 14 | condylar portion |
| 15 | rear surface |
| 16 | conversion module |
| 17 | stem connector |
| 18 | frustroconical portion |
| 19 | connector axis |
| 20 | stem |
| 21 | stem axis |
| 22 | angled stem axis |
| 23 | outer surface |
| 24 | end portion |
| 25 | end portion |
| 26 | end surface |
| 27 | end surface |
| 28 | socket |
| 29 | socket |
| 30 | socket axis |
| 31 | socket axis |
| 33 | conical surface |
| 34 | circular end wall |
| 35 | conical surface |
| 36 | circular end wall |
| 37 | angle |
| 40 | tibial component |
| 41 | articulating surface |
| 42 | articulating surface |
| 43 | polymeric insert |
| 44 | table |
| 45 | connector portion |
| 46 | frustroconical connector |
| 47 | connector axis |
| 48 | axis |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A joint prosthesis for surgical implantation to a patient's intramedullary canal adjacent one of the patient's leg joints comprising;
   a) a joint prosthesis body portion that extends transversely relative to the patient's intramedullary canal for carrying a bearing surface that can articulate with an adjacent bone of the patient or with an adjacent prosthesis component;
   b) a connector on the prosthesis body portion opposite the bearing surface said connector having a linear central axis;
   c) an elongated slender generally cylindrically-shaped stem member of a generally uniform diameter sized and shaped to be contained within the patient's intramedullary canal along a majority of the stem length said stem member having a length many times greater than its diameter, a linear stem longitudinal axis and first and second end portions;
   d) each of said first and second end portions having stem connector means for forming a selected first or second connection between the stem and the body portion at the connector either of a selected one of first or second end portions of the stem; said connector means comprising sockets;
   e) at least one of the stem end portions being so configured that the stem member linear axis forms an acute angle with said connector linear axis upon assembly of said stem and said body portion; and
   f) wherein the central axis of each socket forms an angle of between zero and ten degrees (0°–10°) with the linear axis of the stem.

2. A joint prosthesis for surgical implantation to a patient's intramedullary canal adjacent one of the patient's leg joints comprising;
   a) a joint prosthesis body portion that extends transversely relative to the patient's intramedullary canal for carrying a bearing surface that can articulate with an adjacent bone of the patient or with an adjacent prosthesis component;
   b) a connector on the prosthesis body portion opposite the bearing surface said connector having a linear central axis;
   c) an elongated slender generally cylindrically-shaped stem member of a generally uniform diameter sized and shaped to be contained within the patient's intramedullary canal along a majority of the stem length said stem member having a length many times greater than its diameter and a linear stem longitudinal axis and first and second end portions;
   d) each of said first and second end portions having stem connector means for forming a selected first or second connection between the stem and the body portion at the connector either a selected one of the first or second end portions of the stem;
   e) at least one of the stem end portions being so configured that the stem member linear axis forms an acute angle with said connector linear axis upon assembly of said stem and said body portion; and
   f) wherein the connector is a projection and the stem connector means comprises sockets at the stem ends, each having conical wall portions that can form a connection with the connector.

3. The apparatus of claim 2 wherein the sockets have end wall portions.

4. The apparatus of claim 2 wherein one of the sockets have a central longitudinal axis that forms an angle with the central longitudinal axis of the stem.

5. The apparatus of claim 4 wherein the central longitudinal axis of one of the sockets forms an acute angle of less than ten degrees (10°) with the central longitudinal axis of the stem.

6. The apparatus of claim 1 wherein the joint prosthesis portion includes a conversion module that fits the rear, non-articulating portion of the prosthesis body.

7. The apparatus of claim 6 wherein a conical connector is mounted on the conversion module.

8. A knee, hip or like joint for surgical implantation to a patient's bone adjacent a joint comprising;
   a) a prosthesis body that extends transversely relative to a patient's intramedullary canal for carrying a bearing surface that can articulate with the patient's adjacent leg bone or with another knee prosthesis component;
   b) a prosthesis body connector portion extending from the prosthesis body and along a connector axis;
   c) an elongated slender stem member sized and shaped to be contained within the patient's intramedullary canal along a majority of the stem length, said stem member having a stem axis and first and second end portions, each end portion having stem sockets for forming connection with the body portion at the first connector;
   d) the stem sockets having central longitudinal socket axes that differ from one another;
   e) wherein the assembly of the prosthesis body connector and a stem socket comprises corresponding interlocking and projecting and socket portions; and
   f) wherein each socket forms an angle of between zero and ten degrees (0°–10°) with the central longitudinal axis of the stem.

9. The apparatus of claim 8 wherein the socket has a conical wall.

10. The apparatus of claim 8 wherein the socket has an end wall.

11. The apparatus of claim 8 wherein one of the sockets has a central longitudinal axis that forms an angle with the central longitudinal axis of the stem upon assembly.

12. The apparatus of claim 8 wherein the stem has end portions that are generally flat transverse surfaces.

13. The apparatus of claim 8 wherein the joint prosthesis portion includes a conversion module that fits the rear, non-articulating portion of the prosthesis body.

14. The apparatus of claim 13 wherein a conical connector is mounted on the conversion module.

15. A knee prosthesis for surgical implantation to a patient's leg bone at the hip joint comprising;
   a) a knee prosthesis body portion that extends transversely relative to the patient's intramedullary canal for carrying a bearing surface that can articulate with the patient's leg bone or with an adjacent knee joint prosthesis;
   b) a connector extending from the prosthesis portion and along a connector axis;
   c) an elongated slender stem member sized and shaped to be contained within the patient's intramedullary canal along a majority of the stem length having a stem longitudinal axis and first and second end portions and a stem axis;
   d) each stem member having a socket for connecting to the connector;
   e) each of the sockets having a central longitudinal axis that differs from one another, and at least one of the sockets having a central longitudinal axis that forms an acute angle with the stem axis; and
   f) wherein the central longitudinal axis of each socket forms an angle of between zero and ten degrees (0°–10°) with the central longitudinal axis of the stem.

16. The apparatus of claim 15 wherein the sockets have conical wall portions.

17. The apparatus of claim 15 wherein the sockets have end wall portions.

18. The apparatus of claim 15 wherein the joint prosthesis portion includes a conversion module that fits the rear, non-articulating portion of the prosthesis body.

19. A knee prosthesis for surgical implantation to a patient's leg bone at the hip joint comprising;
   a) a knee prosthesis body portion that extends transversely relative to the patient's intramedullary canal for carrying a bearing surface that can articulate with the patient's leg bone or with an adjacent knee joint prosthesis;
   b) a connector extending from the prothesis portion and along a connector axis;
   c) an elongated slender stem member sized and shaped to be contained within the patient's intramedullary canal along a majority of the stem length having a stem longitudinal axis and first and second end portions and a stem axis;
   d) each stem member having a socket for connecting to the connector;
   e) each of the sockets having a central longitudinal axis that differ from one another, and at least one of the sockets having a central longitudinal axis that forms an acute angle with the stem axis;.
   f) wherein the joint prosthesis portion includes a conversion module that fits the rear, non-articulating portion of the prosthesis body; and
   g) wherein a conical connector is mounted on the conversion module.

* * * * *